United States Patent [19]
Lulai et al.

[11] Patent Number: 5,635,452
[45] Date of Patent: Jun. 3, 1997

[54] SUPPRESSION OF SPROUTING IN STORED POTATOES USING AROMATIC ACIDS

[75] Inventors: Edward C. Lulai; Paul H. Orr, both of East Grand Forks, Minn.; Martin T. Glynn, Grand Forks, N. Dak.

[73] Assignee: The United States of America as represented by the Secretary of Agriculture, Washington, D.C.

[21] Appl. No.: 507,179

[22] Filed: Jul. 26, 1995

[51] Int. Cl.$^6$ ............................................. A01N 37/10
[52] U.S. Cl. .............................................. 504/324; 504/144
[58] Field of Search ................................. 504/324, 144

[56] References Cited

U.S. PATENT DOCUMENTS 5,129,951  7/1992  Vaughn et al. ............................ 71/122

FOREIGN PATENT DOCUMENTS 0394961  10/1990  European Pat. Off. ........ A01N 37/40

OTHER PUBLICATIONS

Mioduszewska, Halina and Bielinska–Czarnecka, Maria, "Influence of ABA and p–coumaric acid on the acid phosphatase activity in potato tubers at the end of their growth, in dormancy and sprouting", *Acta Physiologiae Plantarium*, vol. 7, No. 2, 1985, pp. 95–101.

Rakitin, Yu V. and Khovanskaya, I.V., "Growth inhibiting effect of maleic hydrazide abscisic acid, and p–coumaric acid in intact and isolated sprouts of potato tubers", *Fiziol. Rast (Moscow)*, 1977, 24(I), pp. 153–159, (Agrichemicals, vol. 86, 1977, pp. 155–156).

Sutton, David L., "Notes Influence of Allelopathic Chemicals on Sprouting of Hydrilla Tubers", *J. aquat. Plant Manage.*, 24, 1986, pp. 88–90.

Sekhavat, A., et al., "Preservation of Potatoes and Onions by Irradiation and Chemical treatments", *Food Preservation by Irradiation*, Proceedings of an International Symposium on food Preservation by Irradiation, held in Wageningen, 21–25 Nov. 1977, vol. I, pp. 83–97.

Roushdy, H. M., et al., "Lower radiation Levels for Better Storageability of Potatoes and Onions Using Certain Chemical Treatments", *Radiation Preservation of Food*, Proceedings of a Symposium, held in Bombay, 13–17 Nov. 1972, pp. 105–125.

Schloman, Jr., William W., et al., "Allelopathic Response of Vegetables to Guayle Residue", *Bioresource Technology*, 35, 1991, pp. 191–196.

Naqvi, Himayat H. and Hanson, George P., "Germination and Growth Inhibitors in Guayule (Parthenium Argentatum Gray) Chaff and Their Possible Influence in Seed Dormancy", *Amer. J. Bot.*, 69(6), 1982, pp. 985–989.

Shirsat, S.G., et al., "Evaluation of treatments with hot water, chemicals and ventilated containers to reduce microbial spoilage in irradiated potatoes", *Potato Research*, 34, 1991, pp. 227–231.

Moreland, Donald E. and Novitzky, William P., "Effects of Phenolic Acids, Coumarins, and Flavonoids on Isolated Chloroplasts and Mitochondria", *Allelochemicals Role in Agriculture and Forestry*, Chapter 23, pp. 247–261.

Mandava, N. Bhushan, "Chemistry and Biology of Allelopathic Agents", *The Chemistry of Allelopathy*, pp. 33–54.

Manthem, Barbara, et al., "Effects of Salicyclic Acid on Growth and Stomatal Movements of *Vicia faba* L.: Evidence for Salicyclic Acid Metabolization", *Journal of Chemical Ecology*, vol. 18. No. 9, 1992, pp. 1525–1539.

Raskin, Ilya, "Salicylate, A New Plant Hormone", *Plant Physiol.*, 1992, 99, pp. 799–803.

Kim, Seong–Ryong, et al., "Identification of Methyl Jasmonate and Salicylic Acid Response Elements from the Nopaline Synthase (nos) Promoter", *Plant Physiol.*, 1993, 103, pp. 97–103.

Yalpani, Nasser and Raskins, Ilya, "Salicylic acid: a systemic signal in induced plant disease resistance", *Reviews*, publ. Elsevier Science Publishers Ltd., vol. 1, No. 3, Jun. 1993.

Keys, Nathaniel, "Chemical Treatments, Chilling, Cutting, and Heating Sweet Potato (*Ipomoea batatas L. Lam*) Roots to Increase Sprout Production", *Agriculture, Plant Physiology*, Dissertation Abstracts International vol. 48, No. 01, Jul. 1987, pp. 22–B–23–b.

Kageura, Tsuyoshi, et al., "Potato Sprouting Inhibition", Abstract, Chemical Abstracts, vol. 92, 1980, p. 474, 92:162430s.

Einhelling, F. A., "Mechanisms of Action of Allelochemicals in Allelopathy", Fourth Joint Meeting of the Botanical Society of American and the Canadian Botanical Association, Ames, IA, Aug. 1–5, 1993.

Kim, Sung–Kih, and Park, Nou Pung, "Studies on the Preservation of Potato by Combination of Gamma–Radiation and Chemical", *Kor. J. Food Sci. Technol.*, 1975, vol. 7, No. 3, pp. 159–167.

*Primary Examiner*—Brian M. Burn
*Assistant Examiner*—B. Bembenick
*Attorney, Agent, or Firm*—M. Howard Silverstein; Randall E. Deck; John D. Fado

[57] ABSTRACT

A novel process is described for controlling sprouting in potato tubers by exposure of the tubers to an effective amount of anisic acid, coumaric acid, gallic acid, or mixtures thereof.

15 Claims, No Drawings

SUPPRESSION OF SPROUTING IN STORED POTATOES USING AROMATIC ACIDS

BACKGROUND OF THE INVENTION

1. Field of the Invention

The invention relates to a method for natural suppression of sprouting of stored potatoes.

2. Description of Related Art

Typically, tubers are harvested, allowed to suberize (i.e., allow the "skin" or periderm layer to form over wound areas) at warm temperatures for about 10 days, then gradually cooled down to the storage temperature of about 10° C. For the first 1–2 months after harvest, the tubers remain dormant and exhibit little inclination to sprout. However, after this period the tubers must be chemically treated or refrigerated at very cold temperatures to prevent sprouting from occurring, such sprouting causes numerous deleterious effects to the tubers. These include a loss of fresh weight, the conversion of starch to sugars, and a decrease in the quality and appearance of tubers sold fresh. Sprouts and the surrounding tissue also contain elevated levels of toxic glycoalkaloids, which are not destroyed by cooking.

Although sprouting may be inhibited by cold storage at very low temperatures (slightly above freezing), this technique is not only expensive, but also inflicts other deleterious affects upon the tubers, rendering them unsuitable for processing. As potato tubers age, or when they are subjected to very cold temperatures or other stresses, they convert starch to reducing sugars. The development of reducing sugars in the raw product is very undesirable because the sugars combine via aldol condensations with amino acids during processing to form dark melanoidin pigments. Even small accumulations of reducing sugars in the raw product result in an unacceptably dark and unmarketable finished product.

Chlorpropham (CIPC; 1-methylethyl-3-chlorophenylcarbamate) is currently used to control tuber sprouting throughout the industry. Although CIPC has been used effectively, it has been on the market for over three decades and no replacements or improvements to the technology of sprout control have been made commercially available during this time. In the U.S. and around the world, there is increasing emphasis on replacing synthetic control agents (agricultural chemicals) with natural biological control mechanisms that are safe and more environmentally acceptable.

For many centuries, the Incas of South America and their descendants buried potato tubers in pits that were layered with soil and the leaves of Muna plants that belonged to the mint family Lamiaceae, and the genera Minthostachys and Satureja. This treatment prevented sprouting and excessive fresh weight loss, and repeled insect pests. These Muna plants contain copious amounts of essential oils that are substantially comprised of monoterpenes. Aliaga and Feldheim [*Ernahrung*, 9:254–256 (1985)] and Feldheim ["Practicability and Mode of Action of Quality Storage of Potatoes After Harvest," In Report of a Lecture Given to the German Institute for Quality Research (Plant Nutrition Products), March 1985, 6 pages] reported that the oil from the Muna plants was more effective than CIPC in inhibiting sprouting, fresh weight loss, and the incidence of rotted tuber parts over a period of 120 days. The authors also reported that the main components of the oil, including the monoterpenes α- and β-pinene and limonene, and the oxygenated monoterpenes pulegone and menthone/isomenthone, are effective in this regard.

Currently, several research groups in the United States and Europe are investigating alternative synthetic chemical inhibitors to tuber sprouting [Rama and Narasimham, J. Food Sci. Technol., 24:40–42 (1987)].

Vaughn et al. (U.S. Pat. No. 5,139,562) and Vaughn and Spencer (U.S. Pat. No. 5,129,951) disclosed that the oxygenated monoterpenes cineole, fenchone and menthol, as well as several aromatic aldehydes and alcohols, including thymol, hydrocinnamaldehyde, cuminaldehyde, salicylaldehyde, cinnamaldehyde, and benzaldehyde, may be advantageously used to inhibit potato tuber sprouting, fresh weight loss, rotting, and fungal growth. Vaughn and Spencer also reported that the aromatic acid, benzoic acid, did not inhibit tuber sprouting.

SUMMARY OF THE INVENTION

We have now discovered a novel process for controlling sprouting in potato tubers using naturally occurring compounds. Tuber sprouting may be inhibited by exposure of potato tubers to an effective amount of one or more of the following aromatic acids: anisic acid, coumaric acid, and gallic acid.

In accordance with this discovery, it is an object of this invention to provide an improved method for suppression of tuber sprouting without necrosis or softening of the tuber. It is a further object to provide a method for inhibiting the sprouting of tubers under storage and going to fresh market using compounds applied as liquids, volatiles or fogs.

Another object of this invention is to provide a method for suppression of tuber sprouting using naturally-occurring compounds which have low mammalian toxicity, are rapidly biodegraded, do not impart an unpleasant taste or odor to the treated tubers, and which do not impart disease susceptibility.

Other objects and advantages of the invention will become readily apparent from the ensuing description.

DETAILED DESCRIPTION OF THE INVENTION

The commercial importance of inhibiting sprouting and weight loss of tubers is well known. A need exists for an effective method to inhibit or suppress tuber sprouting which uses a compound that is environmentally acceptable, has low mammalian toxicity, and that does not result in necrosis or softening of the tubers, or impart an unpleasant taste or odor thereto. Equally important, the sprout suppression method must not stress the potatoes and thereby cause negative effects on internal processing quality of the tubers; especially important in this regard, the method must not cause the potatoes to respond with increased sugar levels or cause the processed product to darken in color and become unacceptable for marketing.

According to this invention, there is provided a method for inhibiting sprouting of potato tubers by exposing the tubers to an aromatic acid selected from anisic acid, coumaric acid, and gallic acid. Use of anisic acid is particularly preferred. The acids may be applied singly or in mixtures, in pure or substantially pure form, or optionally in a composition.

Exposure of potato tubers to these acids not only inhibits sprouting, but also inhibits fresh weight loss, and does not increase conversion of starch to sugar, which are commonly associated with sprouting. Moreover, this sprout inhibition may be achieved without adversely effecting final color quality (i.e., darkening) of the processed product which may occur with use of some previously reported sprout inhibitors.

Suitable compositions of the aromatic acids of the invention may be prepared or may be naturally occurring. Naturally occurring compositions include but are not limited to a variety of plant extracts such as guayule bagasse and leaves as a source of anisic acid as described by Schloman and Hilton (1991, Bioresource Technology, 35:191–196). The acids may also be formulated with an inert carrier or solvent such as water, oils or alcohols. While as a practical matter, it is expected that pure or substantially pure anisic, coumaric or gallic acid (or a mixture of two or all three) will be formulated with a carrier, impure acid in naturally occurring compositions may also be formulated with a carrier. The practitioner skilled in the art will recognize that the acid composition may be further formulated with, for example, emulsifying agents, fungicides or insecticides, or even with other sprout inhibitors. Examples of other sprout inhibitors which may be used herewith include, but are not limited to, the above-mentioned CIPC, the aromatic alcohols or aldehydes, or monoterpenes of Vaughn (U.S. Pat. Nos. 5,129,951 and 5,139,562), carvone or naphthalenes such as dimethyl naphthalene (Lewis and Kleinkopf, 1993, Potato Grower of Idaho, 22(7):20–21) the contents of each which are incorporated by reference herein. The addition of jasmonate is particularly advantageous for either or both of providing further sprout control or improving the processing color quality of the treated potato tubers, as described in U.S. patent application Ser. No. 08/147,355, filed Nov. 3, 1993 U.S. Pat. No. 5,436,226 (the contents of which are incorporated by reference herein).

Preferred methods of exposure of the potato tubers to the acids involve exposure to the subject compounds while in a liquid phase. In accordance with a preferred embodiment, the acids are applied directly onto the tubers, such as by dipping the tubers into a solution or emulsion thereof. Due to practical restrictions, when applied in this manner, the tubers should be dipped into the acid solution or emulsion for less than 1 hour, preferably between a few seconds to a few minutes (e.g., less than about 15 minutes). Alternatively, the tubers may be treated by spraying with a solution or emulsion of the acids. Spraying the tubers as the they are passed along a conveyor into holding bins or storage areas would provide one convenient mode of application in this embodiment. The practitioner skilled in the art will recognize that suitable formulations of the acids may optionally include a variety of well known solvents or suspending agents, including, but not limited to water.

In another embodiment, the acids may be applied as a gas or vapor phase. These methods take advantage of the relatively high thermal stability of these compounds, and enjoy the benefit of ease of application over a large volume of tubers. Exposure of the tubers to the acids may be achieved by providing the compounds in liquid or solid form and allowing or causing the same to volatilize into the atmosphere adjacent to or surrounding the tubers. Without being limited thereto, especially favored techniques for enhancing this volatilization include fogging or fuming such as by heating or sonicating a composition of acids in a carrier. Alternatively, but less desirably, the acids may be volatilized by simply passing air or some other inert gas over the compounds. Rather than initially providing the acids in liquid or solid form, they may also be provided as a gas directly admitted into the atmosphere adjacent the tubers.

In yet another alternative embodiment, the acids may be incorporated into a slow release vehicle or carrier, such as by encapsulation or placement in a closed permeable container conventional in the art, to provide a controlled rate of release of the volatiles into the atmosphere over an extended period of time.

Exposure of the tubers to the acids may be initiated at any time after harvest or during the storage of the tubers, such as prior to storage, or prior to dormancy breaking or sprouting. Quite unlike treatment with CIPC, wherein the tubers must be allowed to suberize before they are exposed to the active agent, the tubers may be exposed to these acids immediately after harvest. This early treatment does not impair the wound healing abilities of the tubers.

In accordance with the preferred embodiment, for best processing quality, the tubers should be exposed to the acids prior to breaking dormancy or as early as possible thereafter. Such early exposure maximizes the sprout control effectiveness and maintains the processing quality of the tubers. When storing the tubers in bins under storage conditions currently prevalent in the industry (about 9°–10° C.) or at colder temperatures, the tubers are preferably exposed to the acids shortly after harvest, and exposure may be repeated as needed. While tubers previously held under storage conditions without treatment for long periods of time may also be treated for the purpose of sprout inhibition, the degree of inhibition may be reduced, and the stabilization of processing quality may also be lessened.

Exposure to the acids may be provided at a single occurrence, or alternatively continuously, or intermittently during storage as necessary. Treatment with the acids of this invention does not kill the tubers or permanently impair their ability to sprout, thereby rendering them suitable for use with potatoes intended for seed use. Following storage, the tubers may be removed from exposure to the acids and they will begin to sprout within several days.

The absolute amount of the acids and their concentration in a liquid composition or vapor phase may vary and are selected to provide an effective inhibition of tuber sprouting. An effective amount is defined herein as that quantity of anisic, coumaric and/or gallic acid that significantly inhibits potato tuber sprouting in comparison with untreated tubers. Suitable amounts and concentrations may be readily determined by the practitioner skilled in the art. The actual effective amount may vary with a plurality of factors including: the specific acid used, the mode of application, the length of exposure, the age and variety of the potatoes, the volume of potatoes to be treated, environmental conditions such as temperature, humidity and air flow (affecting volatility and potato metabolic activity), and the vehicle or carrier employed (affecting the release rate of the acids into the atmosphere).

Without being limited thereto, the generally preferred concentration of the acids for providing inhibition of sprouting of potato tubers is greater than or equal to about 0.001 mM, with concentrations greater than or equal to about 0.01 or 0.1 mM, and especially about 1.0 mM, being particularly preferred. While it is envisioned that lower amounts may also be effective, the degree of sprout inhibition may be substantially reduced.

The following examples are intended only to further illustrate the invention and are not intended to limit the scope of the invention which is defined by the claims.

EXAMPLE 1

Potato tubers were treated with various levels of anisic acid, coumaric acid, gallic acid, or with CIPC, to demonstrate the effectiveness of the acids as sprout inhibitors.

Potatoes (*Solanum tuberosum*, cv. Norchip) for these tests were grown at the Potato Research Farm, Grand Forks County, N.D., under conventional practices. After harvest, about 20 lbs. of potatoes (approximately 46 tubers) without physical defects were selected for treatment in each test group. Tubers were exposed to test compounds by dipping. Test groups were selected as follows: tubers exposed to one of three levels of p-anisic acid, p-coumaric acid, or gallic acid (1.0 mM, 0.1 mM or 0.01 mM), tubers exposed to 1% CIPC (47 mM), and untreated tubers as a negative control.

It is understood that the foregoing detailed description is given merely by way of illustration and that modifications and variations may be made therein without departing from the spirit and scope of the invention.

TABLE 1

Effect of Aromatic Acids on Suppression of Potato Sprouting When Applied as a Liquid Dip to Freshly Harvested Tubers.

| Treatment | Weeks until sprouting occurred at various suppressant concentrations | | | Agtron color values* | | |
| --- | --- | --- | --- | --- | --- | --- |
| | mM concentrations | | | | | |
| | 1.0 | 0.1 | 0.01 | 1.0 | 0.1 | 0.01 |
| Control | 6 | 6 | 6 | 54 | 54 | 54 |
| Chlorpropham (CIPC) | 15 | 15 | 15 | 55 | 55 | 55 |
| Anisic Acid | 15 | 12 | 9 | 51 | 52 | 52 |
| Coumaric Acid | 12 | 12 | 10 | 54 | 52 | 52 |
| Gallic Acid | 9 | 7 | 6 | 50 | 50 | 52 |

*values are not significantly statistically different

Active agent was suspended in an aqueous solution (using 0.25% Triton X-100) at the appropriate concentration. Tubers were rolled in a shallow pan having about 2.5 cm depth of the test compound, allowed to drip dry, and placed into 15 l glass storage jars (Libby Glass Co., Toledo, Ohio) equipped with inlet and exhaust tubes, about 45–46 tubers per jar. Jars were not ventilated for 24 hr.

All storage jars from each test group were placed in walk-in controlled environment rooms at 8°–10° C. to reflect full-scale potato storage environmental conditions. After the first 24 hours, the jars were continuously ventilated with humidified fresh air (85–95% relative humidity) throughout the course of the experiment, the air in each jar being exchanged every 3–4 hours.

The tubers in each vessel were monitored for sprout growth weekly following jar filling, and the number of tubers having sprouts counted. The results are shown in Table 1, and demonstrate that anisic, coumaric and gallic acid effectively suppress sprouting at lower concentrations than CIPC. The degree of suppression achieved with anisic and coumaric acid was comparable with that obtained with CIPC.

The potato tubers were also examined for processed color quality. Once sprouting was observed, tubers were removed from the jar and processed into chips, and evaluated for processed color quality by measurement of Agtron color reflectance values for fried chips. These results are also shown in Table 1. Agtron reflectance values (ranging from 0–100) indicate better (lighter) processed product color quality with higher Agtron readings. Fried chips from acid treated tubers exhibited substantially the same product color as chips from CIPC treated tubers.

EXAMPLE 2

Another variety of potatoes having a different dormancy period (*Solanum tuberosum*, cv. Russet Burbank) was treated with 0.01 mM anisic acid using the same procedure described in Example 1. Treated tubers exhibited substantially reduced sprouting relative to control (untreated) tubers, sprouting at 20 weeks vs. 14 weeks, respectively. The processed product colors for tubers treated with anisic acid were the same as those for untreated and CIPC treated samples.

We claim:

1. A method for inhibiting sprouting of potato tubers comprising exposing potato tubers to an aromatic acid selected from the group consisting of anisic acid, gallic acid and mixtures thereof, in an amount effective to inhibit sprouting.

2. A method as described in claim 1 wherein said aromatic acid is anisic acid.

3. A method as described in claim 1 wherein said aromatic acid is substantially pure.

4. A method as described in claim 1 wherein said aromatic acid is in a composition with a carrier.

5. A method as described in claim 1 wherein said exposing comprises contacting said tubers with said aromatic acid in a liquid phase.

6. A method as described in claim 5 wherein said contacting comprises dipping said tubers into a solution or emulsion of said aromatic acid.

7. A method as described in claim 1 further comprising exposing said tubers to a second sprout inhibiting agent.

8. A method as described in claim 7 wherein said second sprout inhibiting agent is selected from the group consisting of jasmonates, CIPC, aromatic alcohols, aromatic aldehydes, monoterpenes, carvone and naphthalenes.

9. A method for inhibiting sprouting of potato tubers comprising exposing potato tubers to an aromatic acid selected from the group consisting of anisic acid, coumaric acid, gallic acid and mixtures thereof, in an amount effective to inhibit sprouting, and wherein said exposing is selected from the group consisting of:

a) contacting said tubers with said aromatic acid in a liquid phase by direct liquid application for less than 1 hour;

b) contacting said tubers with said aromatic acid in a gas phase; and c) contacting said tubers with said aromatic acid in a vapor phase.

10. A method as described in claim 9 wherein said exposing comprises contacting said tubers with said aromatic acid in said liquid phase by said direct liquid application for less than 1 hour.

11. A method as described in claim 9 wherein said exposing comprises contacting said tubers with said aromatic acid in said gas phase.

12. A method as described in claim 9 wherein said exposing comprises contacting said tubers with said aromatic acid in said vapor phase.

13. A method as described in claim 12 wherein said vapor phase is a fog.

14. A method as described in claim 9 further comprising exposing said tubers to a second sprout inhibiting agent.

15. A method as described in claim 14 wherein said second sprout inhibiting agent is selected from the group consisting of jasmonates, CIPC, aromatic alcohols, aromatic aldehydes, monoterpenes, carvone and naphthalenes.

* * * * *